(12) United States Patent
Lee

(10) Patent No.: US 11,571,029 B2
(45) Date of Patent: Feb. 7, 2023

(54) WRIST GUARD WITH IMPROVED OPERATION PERFORMANCE

(71) Applicant: Sang Jin Lee, Gyeongsangnam-do (KR)

(72) Inventor: Sang Jin Lee, Gyeongsangnam-do (KR)

( * ) Notice: Subject to any disclaimer, the term of this patent is extended or adjusted under 35 U.S.C. 154(b) by 448 days.

(21) Appl. No.: 16/955,663

(22) PCT Filed: Oct. 17, 2018

(86) PCT No.: PCT/KR2018/012237
§ 371 (c)(1),
(2) Date: Jun. 18, 2020

(87) PCT Pub. No.: WO2019/124698
PCT Pub. Date: Jun. 27, 2019

(65) Prior Publication Data
US 2020/0383401 A1    Dec. 10, 2020

(30) Foreign Application Priority Data
Dec. 18, 2017  (KR) .................. 10-2017-0174371

(51) Int. Cl.
*A41D 13/08*    (2006.01)
*A61F 5/32*    (2006.01)
(Continued)

(52) U.S. Cl.
CPC ............ *A41D 13/088* (2013.01); *A61F 2/585* (2013.01); *A61F 5/0118* (2013.01);
(Continued)

(58) Field of Classification Search
CPC .............. A41D 13/088; A41D 2400/32; A41D 13/081; A41D 13/08; A41D 13/05;
(Continued)

(56) References Cited

FOREIGN PATENT DOCUMENTS

DE         7037181 U      1/1971
JP         2011-528569    11/2011
(Continued)

OTHER PUBLICATIONS

International Search Report for PCT/KR2018/012237 dated Mar. 28, 2019 and its English translation from WIPO (now published as WO2019/124698).
(Continued)

*Primary Examiner* — Tarla R Patel
(74) *Attorney, Agent, or Firm* — Revolution IP, PLLC

(57) ABSTRACT

Provided is a wrist guard designed to press the radial and ulnar parts of a wrist toward the center of the wrist by means of a compression pad, so as to prevent side effects, such as hand numbness and swelling and effectively provide a fixing force of the wrist, thereby preventing the wrist from being excessively bent and alleviating wrist pain. The wrist guard allows a user to adjust the pressure load on the radial and ulnar parts of the wrist. It is possible to smoothly insert and assemble the pressing member into a coupling body, therefore improving operational feeling, the wrist guard may be stably used, and damage due to interference can be prevented. A stable pulling operation prevents wear and damage. As an excessive pressure load on the radial and ulnar regions is attenuated, the wrist guard is more convenient and comfortable.

6 Claims, 8 Drawing Sheets

(51) Int. Cl.
*A61F 5/01* (2006.01)
*A61F 2/58* (2006.01)
*A61F 5/058* (2006.01)

(52) U.S. Cl.
CPC ............ *A61F 5/05866* (2013.01); *A61F 5/32* (2013.01); *A41D 2400/32* (2013.01)

(58) Field of Classification Search
CPC ......... A41D 13/00; A61F 5/0118; A61F 5/32; A61F 5/0102; A61F 5/01; A61F 5/00; A61F 5/058; A61F 5/05841; A61F 5/05858; A61F 5/05866; A61F 5/05875
See application file for complete search history.

(56) References Cited

FOREIGN PATENT DOCUMENTS

| KR | 20-0448284 | | 3/2010 | |
|---|---|---|---|---|
| KR | 10-1559109 | | 10/2015 | |
| KR | 10-1607695 | | 3/2016 | |
| KR | 101837187 | B1 * | 11/2016 | |
| KR | 30-0923966 | | 9/2017 | |
| KR | 10-1892573 | | 8/2018 | |
| WO | 99-00076 | A1 | 1/1999 | |
| WO | WO-9900076 | A1 * | 1/1999 | ............ A61F 5/0118 |

OTHER PUBLICATIONS

Written Opinion of the International Searching Authority for PCT/KR2018/012237 dated Mar. 28, 2019 and its English translation from WIPO (now published as WO2019/124698).

* cited by examiner

WRIST GUARD WITH IMPROVED OPERATION PERFORMANCE

CROSS-REFERENCE TO RELATED APPLICATIONS

The present application is the U.S. National Phase of PCT Application No. PCT/KR2018/012237 filed on Oct. 17, 2018, which claims the priority to Korean Patent Application No. 10-2017-0174371 filed on Dec. 18, 2017, the entire contents of which are incorporated herein by reference.

TECHNICAL FIELD

The present disclosure relates to a wrist guard. More particularly, the present disclosure relates to a wrist guard, in which compression pads are used to compress only the ulna area and the radius area of the wrist toward the center of the wrist, thereby preventing side effects, such as hand numbness or hand swelling. In addition, fixing force of the wrist may be effectively supplemented to prevent the wrist from being excessively bent and reduce pain in the wrist. A compressive load applied to the ulna area and the radius area of the wrist may be adjusted. A compression member may be smoothly fitted into a coupling body to improve the feel of operation, enable the wrist guard to be reliably used, and prevent damage caused by interference. A pulling operation of a connecting wire for pulling the compression member may be reliably carried out to prevent the abrasion and damage of the connecting wire. An excessive compressive load to the ulna area and the radius area may be relieved to improve the convenience and comfort of wearing of the wrist guard.

BACKGROUND ART

Regarding the joints of an arm of a human body, the radius and the ulna constitute the forearm, eight (8) carpal bones constitute the wrist, five (5) metacarpal joints by which pivoting, flexing, and extension are enabled constitute the palm, and phalangeal bones constitute each finger while providing a function of gripping an object to the finger.

Such joints may be injured by repeated and continuous excessive use thereof due to operations of holding objects with hands or due to activities. In some cases, injured joints may not be completely healed and chronic pain may occur.

Therefore, wrist guards respectively attached to a wrist of a human body to protect such joints and bones have been proposed and used.

In general, a wrist guard, together with an elbow protector, an ankle protector, a forearm protector, and the like, is attached to a frail joint portion of a person to protect the joint portion. The wrist guard is attached to athletes playing various sports games, workers, or children enjoying games.

A typical wrist protector of the related art has the shape of a band surrounding the wrist, and is placed along the outer surface of the wrist to uniformly compress the wrist and portions adjacent to the wrist. The wrist protector serves to protect the wrist by compressing the wrist and prevent the wrist from being excessively bent.

However, because a wrist protector of the related art uniformly compresses the entire area of the wrist, if the wrist protector has been attached to the wrist for an extended period of time, blood may not flow through the wrist artery properly, thereby causing the hand to tingle or swell, which is problematic. Due to such a problem, such as hand numbness, the use of the wrist protector is limited. For example, a user may remove the wrist protector during or before driving. Accordingly, the wrist may be exposed to the danger of an injury during a variety of exercises or activities, instead of being safely protected.

DISCLOSURE

Technical Problem

The present disclosure has been made in consideration of the above-described problems occurring in the related art, and an objective of the present disclosure is to provide a wrist guard able to compress only the ulna area and the radius area of the wrist toward the center of the wrist using compression pads in order to prevent side effects, such as hand numbness or hand swelling. The use of the compression pads may also supplement fixing force of the wrist in order to reliably perform a wrist protecting function of, for example, preventing the wrist from being excessively bent and reducing pain in the wrist.

Another objective of the present disclosure is to provide a wrist guard in which a compression member configured such that portions of the compression member are to be pivotably coupled to each other and the coupling force between the portions of the compression member is adjusted by user operation, so that a compressive load applied to the ulna area and radius area of the wrist may be adjusted. Accordingly, the wrist guard may be more conveniently and optimally used according to user requirements.

Another objective of the present disclosure is to provide a wrist guard in which the compression member includes a main ring body made of an elastically deformable material and a connecting body made of a rigid material, the main ring body and the connecting body being pivotably coupled to each other. In response to a pulling operation of a connecting wire, the compression member may be smoothly fitted together, thereby improving the feel of operation and enabling the wrist guard to be reliably used. In addition, damage caused by interference may be prevented, thereby improving the durability of the wrist guard.

Another objective of the present disclosure is to provide a wrist guard in which a guide through-hole is formed in the connecting body of the compression member and has a curved path guiding the connecting wire to extend through the connecting body. When the connecting wire is pulled through the guide through-hole, the connecting wire may move smoothly, so that the pulling operation of the connecting wire may be reliably carried out, thereby minimizing abrasion and damage to the connecting wire.

Another object of the present disclosure is to provide a wrist guard in which a plurality of through-holes are formed in the central portions of the compression pads. Even when the compression pads apply an excessive compressive load to the ulna area and the radius area, the compression pads may be elastically deformed due to the through-holes to relieve the excessive compressive load, thereby improving the convenience and comfort of wearing of the wrist guard.

Technical Solution

According to an aspect of the present disclosure, provided is a wrist guard attached to a wrist to protect the wrist. The wrist guard may include: a compression member surrounding a wrist, wherein a first compression pad is provided on one portion of an inner surface of the compression member to be able to compress one of an ulna area and a radius area of the wrist toward a central portion of the wrist, and a second compression pad is provided on the other portion of the inner surface of the compression member to be able to compress the other of the ulna area and the radius area of the wrist toward the central portion of the wrist; and a coupling body, wherein one end portion of the compression member is pivotably coupled to one portion of the coupling body, and the other end portion of the compression member is coupled to or decoupled from the other end portion of the coupling body in response to user operation, wherein the wrist, other than the ulna area and the radius area, is not compressed, and a coupling state of the second compression member is adjustable by the user operation so that compressive load of the compression member on the ulna area and the radius area is adjustable.

Here, the compression member may include: a main ring body made of an elastically deformable material and having a shape of a ring with one open portion, the first compression pad and the second compression pad being mounted on inner surface portions of the main ring body, wherein one end portion of the main ring body is pivotably coupled to one portion of the coupling body; a connecting body pivotably coupled to the other end portion of the main ring body, wherein the connecting body is coupled to or decoupled from the other portion of the coupling body.

In addition, the connecting body may be made of a rigid material that is less elastically deformable than the main ring body.

The other end portion of the coupling body may have an insertion guide hole allowing the other end portion of the compression member to be inserted thereinto and coupled thereto. A manipulator operable by a user may be disposed on a central portion of the coupling body. A depth, to which the other end portion of the compression member is inserted into the insertion guide hole, may be adjusted by the manipulator.

A connecting wire may be coupled to, while extending through, a distal end of the connecting body, and the connecting wire may be pulled by operating the manipulator, so that the connecting body is inserted into and coupled to the insertion guide hole.

The connecting body may have a guide through-hole to guide a path along which the connecting wire is coupled to, while extending through, the connecting body, and the guide through-hole may have a curved path convex in a direction opposite to a pulling direction of the connecting wire.

The manipulator may include: a fixed body fixedly coupled to the coupling body and having a ratchet provided on an inner circumferential portion of a top end portion thereof; rotary body coupled to the fixed body so as to be movable and rotatable in top-bottom direction and having a stopper protrusion provided on one portion thereof, wherein the stopper protrusion engages with the ratchet to restrain undirectional rotation in downward movement, and engagement of the stopper protrusion and the ratchet is released in upward movement so as to enable bidirectional rotation; and a dial knob coupled to an upper portion of the rotary body to move in a top-bottom direction and rotate together with the rotary body, the dial knob being operable by the user. The connecting wire coupled to, while extending through, the connecting body may be wound on the rotary body in a single direction.

The first compression pad and the second compression pad may extend along predetermined longitudinal portions of the compression member, with through-holes penetrating through central portions of the first and second compression pads in a transverse direction.

The plurality of through-holes of the first and second compression pads may be spaced apart from each other in a longitudinal direction of the compression member.

Advantageous Effects

According to the present disclosure, the wrist guard may be used to compress only the ulna area and the radius area of the wrist toward the center of the wrist using compression pads in order to prevent side effects, such as hand numbness or hand swelling. The use of the compression pads may also supplement fixing force of the wrist in order to reliably perform a wrist protecting function of, for example, preventing the wrist from being excessively bent and reducing pain in the wrist.

In addition, the compression member is configured such that portions of the compression member are to be pivotably coupled to each other and the coupling force between the portions of the compression member is adjusted by user operation, so that a compressive load applied to the ulna area and radius area of the wrist is adjustable. Accordingly, the wrist guard may be more conveniently and optimally used according to user requirements.

The compression member includes the main ring body made of an elastically deformable material and the connecting body made of a rigid material. The main ring body and the connecting body are pivotably coupled to each other. In response to the pulling operation of the connecting wire, the compression member may be smoothly fitted together, thereby improving the feel of operation and enabling the wrist guard to be reliably used. In addition, damage caused by interference may be prevented, thereby improving the durability of the wrist guard.

The guide through-hole is formed in the connecting body of the compression member and has a curved path guiding the connecting wire to extend through the connecting body. When the connecting wire is pulled through the guide through-hole, the connecting wire may move smoothly, so that the pulling operation of the connecting wire may be reliably carried out, thereby minimizing abrasion and damage to the connecting wire.

The plurality of through-holes are formed in the central portions of the compression pads. Even when the compression pads apply an excessive compressive load to the ulna area and the radius area, the compression pads may be elastically deformed due to the through-holes to relieve the excessive compressive load, thereby improving the convenience and comfort of wearing of the wrist guard.

BEST MODE

Figure 1:
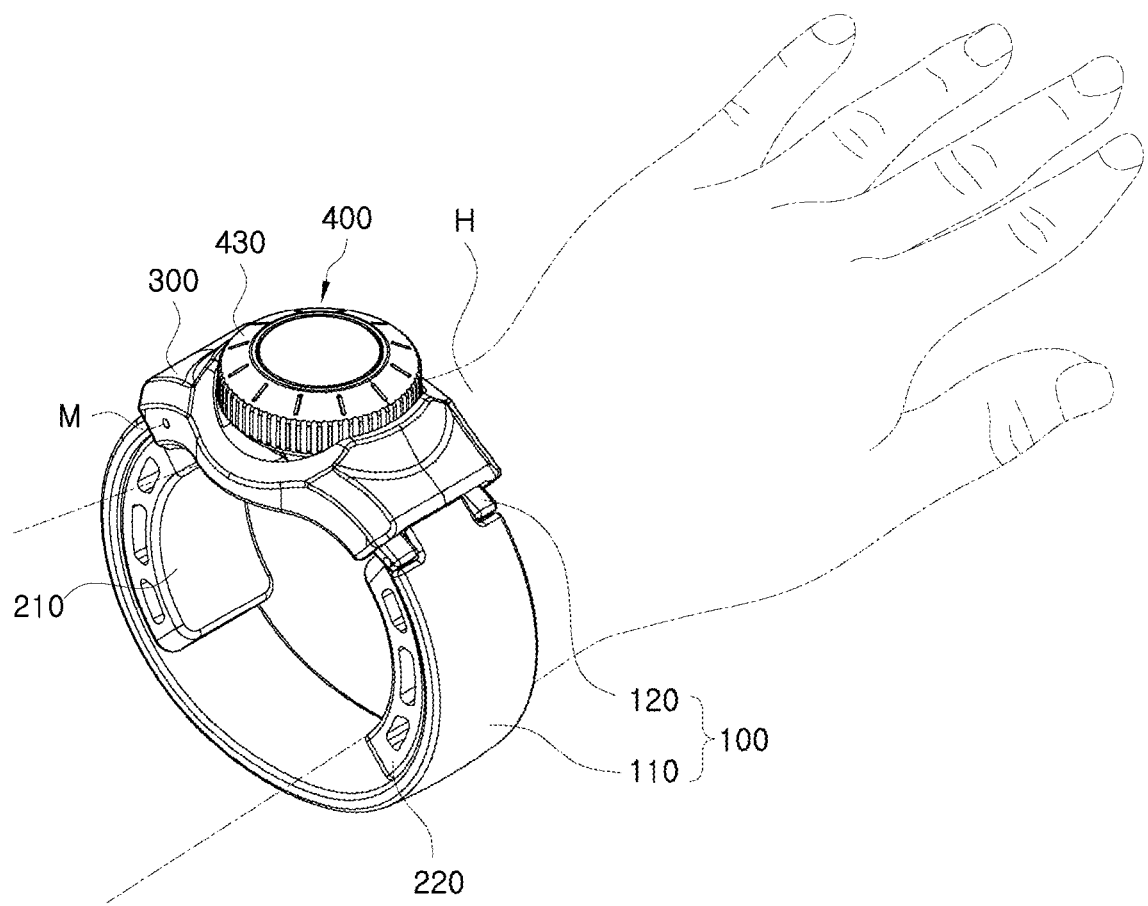
FIG. 1 is a perspective view schematically illustrating the shape of a wrist guard according to embodiments of the present disclosure.

Hereinafter, embodiments of the present disclosure will be described in detail with reference to the accompanying drawings. Throughout this document, reference should be made to the drawings, in which the same reference numerals and symbols will be used to designate the same or like components. In the following description of the present disclosure, detailed descriptions of known functions and components incorporated herein will be omitted in the case that the subject matter of the present disclosure may be rendered unclear thereby.

Figure 2:
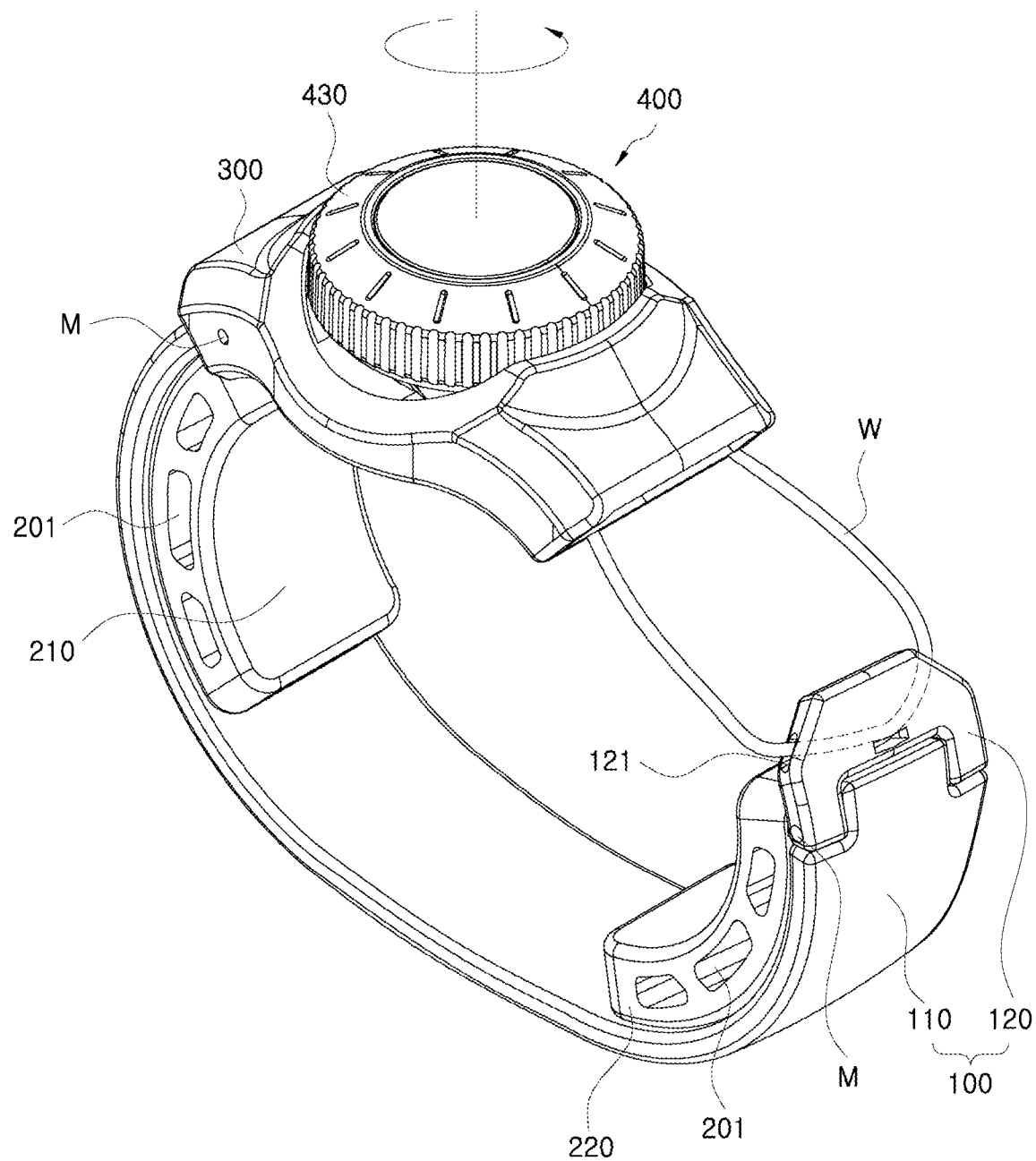
FIG. 2 is a perspective view schematically illustrating the detached state of the wrist guard according to embodiments of the present disclosure.
Figure 3:
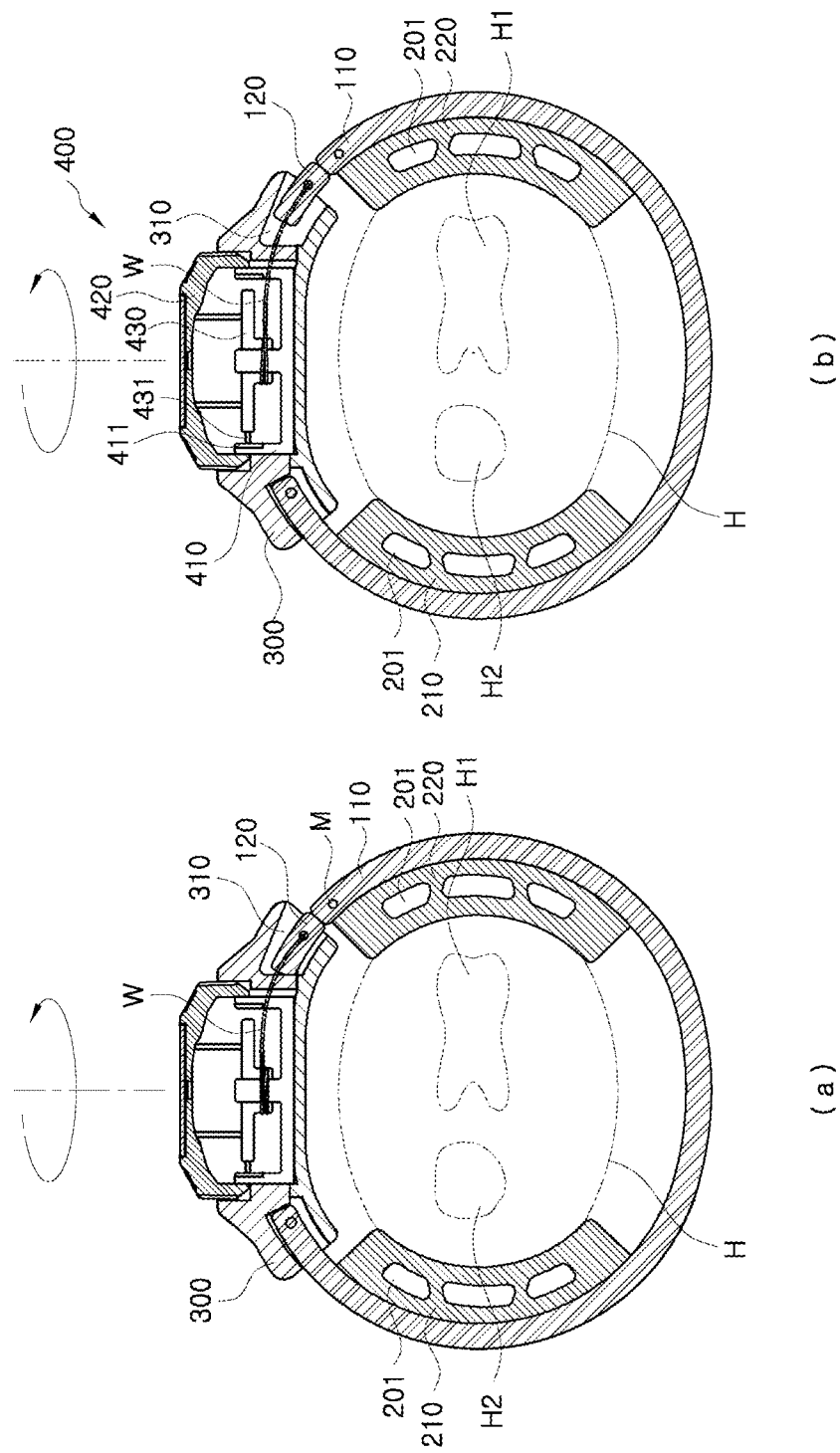
FIG. 3 schematically illustrates compressive load adjusting states of the wrist guard according to embodiments of the present disclosure.
Figure 4:
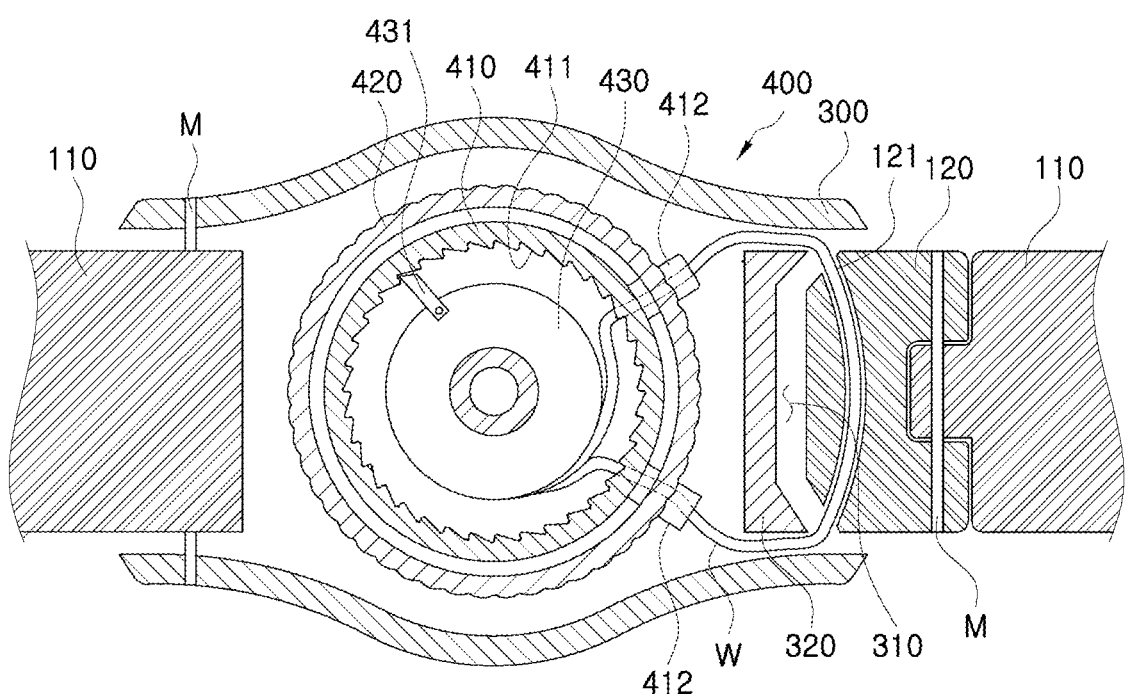
FIG. 4 is a cross-sectional view schematically illustrating an internal structure of an operating portion of the wrist guard according to embodiments of the present disclosure.

FIG. 1 is a perspective view schematically illustrating the shape of a wrist guard according to embodiments of the present disclosure, FIG. 2 is a perspective view schematically illustrating the detached state of the wrist guard according to embodiments of the present disclosure, FIG. 3 schematically illustrates compressive load adjusting states of the wrist guard according to embodiments of the present disclosure, and FIG. 4 is a cross-sectional view schematically illustrating an internal structure of an operating portion of the wrist guard according to embodiments of the present disclosure.

The wrist guard according to embodiments of the present disclosure is attachable to a wrist H of a user to reliably protect a wrist without side effects, such as hand numbness. The wrist guard includes a compression member 100, on which a first compression pad 210 and a second compression pad 220 are mounted, and a coupling body 300.

The compression member 100 may be configured to surround the wrist H, have the shape of a ring with one portion thereof being open, and be made of an elastically deformable material. The first compression pad 210 is mounted on one portion of the inner surface of the compression member 100 to compress one of the area of the ulna H1 and the area of the radius H2 of the wrist toward the center of the wrist. The second compression pad 220 is mounted on the other portion of the inner surface of the compression member 100 to compress the other of the area of the ulna H1 and the area of the radius H2 of the wrist toward the center of the wrist.

For example, the first compression member 110 may be disposed to compress the area of the radius H2 of the wrist toward the center of the wrist while surrounding the area of the radius H2, while the second compression member 120 may be disposed to compress the area of the ulna H1 of the wrist H toward the center of the wrist while surrounding the area of the ulna H1.

The coupling body 300 is configured such that one end portion of the compression member 100 is pivotably coupled to one portion of the coupling body 300 and the other end portion of the compression member 100 is coupled to or decoupled from the other portion of the coupling body 300 in response to user operation.

In the wrist guard configured as above, the first compression pad 210 and the second compression pad 220 of the compression member 100 compress the area of the ulna H1 and the area of the radius H2 of the wrist H. Here, the wrist guard is configured such that the wrist H, other than the area of the ulna H1 and the area of the radius H2, is not compressed thereby. That is, the wrist guard may be configured such that the portions of the wrist guard, other than the area of the ulna H1 and the area of the radius H2, are in simple contact with the wrist H, instead of being spaced apart from the wrist H or compressing the wrist H.

Accordingly, since the area of the ulna H1 and the area of the radius H2 of the wrist H are compressed by the first compression pad 210 and the second compression pad 220, the wrist guard according to embodiments of the present disclosure may supplement the fixing force of the wrist H to reliably perform a wrist protecting function of, e.g. preventing the wrist from being excessively bent or reducing pain in the wrist. Here, no portions of the wrist H, other than the area of the ulna H1 and the area of the radius H2, are compressed by the first compression pad 210 or the second compression pad 220 to obstruct the circulation of blood. Accordingly, no side effects, such as hand numbness or hand swelling, may occur.

In addition, health supplement members (not shown) made of zirconium (Zr), germanium (Ge), or the like may be inserted into the first compression pad 210 and the second compression pad 220 in order to apply a variety of health supplement functions to the wrist.

In addition, the first compression pad 210 and the second compression pad 220 extend along predetermined longitudinal portions of the compression member 100. A plurality of through-holes 201 may be configured to penetrate through the central portions of the first compression pad 210 and the second compression pad 220 in the transverse direction. The plurality of through-holes 201 may be spaced apart from each other in the longitudinal direction of the compression member 100. Due to the through-holes 201, the first compression pad 210 and the second compression pad 220 may be easily elastically deformed while compressing the ulna area and the radius area. Accordingly, even when the wrist is excessively compressed during the use of the wrist guard, the first compression pad 210 and the second compression pad 220 may be elastically deformed due to the through-holes 201, thereby relieving a compressive load.

In addition, one end portion of the compression member 100 is pivotably coupled to one portion of the coupling body 300, and the other end portion of the compression member 100 is disposed to be coupled to or decoupled from the other portion of the coupling body 300. Here, the compression member 100 is configured such that the coupling state thereof may be adjusted by the user operation, so that the compressive load of the first compression pad 210 and the second compression pad 220 on the area of the ulna H1 and the area of the radius H2 is adjusted.

More specifically, the other end portion of the coupling body 300 has an insertion guide hole 310 allowing the other end portion of the compression member 100 to be inserted thereinto, so that the compression member 100 is coupled to the coupling body 300. A manipulator 400 operable by the user is disposed on the central portion of the coupling body 300. The manipulator 400 is configured such that a depth to which the other end portion of the compression member 100 is inserted into the insertion guide hole 310 may be adjusted using the manipulator 400.

Here, a separate connecting wire W may be coupled to, while extending through, the other end portion of the compression member 100 to be connected to the manipulator 400 of the coupling body 300. The connecting wire W may be pulled by operating the manipulator 400 so that the other end portion of the compression member 100 is inserted into the insertion guide hole 310.

According to this configuration, the manipulator 400 of the coupling body 300 may be operated to release the connecting wire W from the pulled position, so that the other end portion of the compression member 100 is decoupled from the coupling body 300 as illustrated in FIG. 2. In contrast, the connecting wire W may be pulled by operating the manipulator 400 of the coupling body 300, so that the other end portion of the compression member 100 is coupled to the coupling body 300 as illustrated in FIG. 1.

Since the other end portion of the compression member 100 is connected to the coupling body 300 via the connecting wire W even after the second compression member 120 is decoupled from the coupling body 300, the wrist guard as described above constantly maintains the overall shape of a ring. In an open position in which the other end portion of the compression member 100 is decoupled from the coupling body 300 as illustrated in FIG. 2, after the wrist is located in the direction of penetration of the internal space of the wrist guard, the connecting wire W may be pulled by operating the manipulator 400, so that the wrist H is compressed as illustrated in FIG. 1.

Here, the compression member 100 may be elastically deformed while pivoting about a rotary shaft M of the coupling body 300 of the compression member 100, so that the entire internal space of the wrist guard is expanded or contracted. Thus, when the wrist H is inserted into or removed from the internal space of the wrist guard, the wrist H may be more conveniently moved.

In addition, as the depth to which the other end portion of the compression member 100 is inserted into the insertion guide hole 310 is adjusted by operating the manipulator 400, the compressive load on the area of the ulna H1 and the area of the radius H2 of the first compression pad 210 and the second compression pad 220 is adjusted. For example, as illustrated in (a) in FIG. 3, when the manipulator 400 is operated so that the other end portion of the compression member 100 is inserted relatively deeply into the insertion guide hole 310, the compressive load of the first compression pad 210 and the second compression pad 220 on the area of the ulna H1 and the area of the radius H2 relatively increases. As illustrated in (b) in FIG. 3, when the manipulator 400 is operated so that the other end portion of the compression member 100 is inserted relatively shallowly into the insertion guide hole 310, the compressive load of the first compression pad 210 and the second compression pad 220 on the area of the ulna H1 and the area of the radius H2 relatively decreases.

The compression member 100 may include a main ring body 110 and a connecting body 120 provided separately from the main ring body 110 as illustrated in FIGS. 1 and 2, although the compression member 100 may be provided as a single ring-shaped structure that is elastically deformable.

The main ring body 110 is made of an elastically deformable material, in the shape of a ring with one portion thereof being open. The first compression pad 210 and the second compression pad 220 are mounted on the inner surface of the main ring body 110. One end portion of the main ring body 110 is pivotably coupled to one portion of the coupling body 300. The connecting body 120 is pivotably coupled to the other end portion of the main ring body 110, and is configured to be inserted into and coupled to the insertion guide hole 310 of the coupling body 300. Here, the rotary shaft M of the connecting body 120 extends perpendicularly to the longitudinal direction of the main ring body 110. The connecting body 120 is made of a rigid material that is less elastically deformable than the main ring body 110. For example, the main ring body 110 may be made of a urethane material, while the connecting body 120 may be made of a rigid plastic material. In addition, the connecting wire W to be pulled by the manipulator 400 is configured such that the connecting wire W extends through a distal end of the connecting body 120 to pull the connecting body 120.

As described above, the compression member 100 is comprised of the main ring body 110 and the connecting body 120 separate from the main ring body 110. Thus, the compression member 100 may be easily inserted into the insertion guide hole 310 of the coupling body 300.

Specifically, the other end portion of the compression member 100 is pulled by the connecting wire W to be inserted into the insertion guide hole 310 of the coupling body 300. In a case in which the compression member 100 is provided as a single body, the direction of the other end of the compression member 100 may differ from the pulling direction of the connecting wire W by a predetermined angle. Thus, interference may occur during insertion of the other end portion of the compression member 100 into the insertion guide hole 310 of the coupling body 300. Due to such interference, the operation may not be smooth and the feel of operation may be reduced. In addition, when used for a long period of time, the corresponding portions or components may be damaged, which is problematic.

According to an embodiment, in the compression member 100, the connecting body 120 made of a rigid material is pivotably coupled to a distal end of the ring-shaped main ring body 110 on which the first compression pad 210 and the second compression pad 220 are mounted, and the connecting wire W is coupled to, while extending through, the distal end of the connecting body 120. Due to this configuration, when the other end portion of the compression member 100, i.e. the connecting body 120, is pulled by the connecting wire W, the connecting body 120 rotates about the rotary shaft M due to the pulling force of the connecting wire W to be oriented in the same direction as the pulling direction of the connecting wire W. Accordingly, the connecting body 120 is smoothly inserted into the insertion guide hole 310 of the coupling body 300 without interference.

In addition, the connecting wire W is coupled to, while extending through, the connecting body 120. In this regard, the connecting body 120 has a guide through-hole 121 to guide a path, along which the connecting wire W is coupled to, while extending through, the connecting body 120. The guide through-hole 121 is configured to penetrate through the connecting body 120 in the transverse direction of the connecting body 120. Here, the guide through-hole 121 has a curved path convex in a direction opposite to the pulling direction of the connecting wire W, instead of having a linear path.

Since the guide through-hole 121 is configured to have a curved path as described above, the connecting wire W may move smoothly along the guide through-hole 121 while being pulled, so that the pulling operation may be smoothly carried out. Accordingly, friction or the like caused by the movement of the connecting wire W may be minimized to prevent abrasion and damage.

In addition, the manipulator 400 includes a fixed body 410, a rotary body 430, and a dial knob 420. The fixed body 410 is fixedly coupled to the coupling body 300, and has a ratchet 411 provided on the inner circumference of the top end portion of the fixed body 410. The rotary body 430 is coupled to the fixed body 410 so as to be movable and rotatable in a top-bottom direction. A stopper protrusion 431 provided on one portion of the rotary body 430 engages with the ratchet 411 to restrain unidirectional rotation in the case of downward movement. In the case of upward movement, the engagement of the stopper protrusion 431 and the ratchet 411 is released to enable bidirectional rotation. The dial knob 420 is coupled to the upper portion of the rotary body 430 to move in a top-bottom direction and rotate together with the rotary body 430, and is configured to be operated by the user. The connecting wire W coupled to, while extending through, the connecting body 120 is configured to be wound on the rotary body 430 in one direction.

Accordingly, in a position in which the dial knob 420 is moved downwardly by pressure, when the dial knob 420 is rotated, for example, in the clockwise direction, the rotary body 430 rotates together with the dial knob 420, and the connecting wire W is wound on the rotary body 430. Consequently, the connecting wire W is pulled toward the coupling body 300, so that the second compression member 120 is inserted into and coupled to the insertion guide hole 310. In this position, the stopper protrusion 431 is engaged with the ratchet 411 of the fixed body 410, thereby restraining the rotation of the rotary body 430 in the opposite direction. Accordingly, in response to the dial knob 420 being operated to rotate, the second compression member 120 is continuously and more deeply inserted into the insertion guide hole 310, so that the compression load on the area of the ulna H1 and the area of the radius H2 is increased, and remains in this position.

In contrast, to reduce the compression load on the area of the ulna H1 and the area of the radius H2 or to decouple the second compression member 120 from the coupling body 300, the dial knob 420 may be pulled upwardly to decouple the stopper protrusion 431 of the rotary body 430 from the ratchet 411 of the fixed body 410. In this position, the second compression member 120 may be rotated and moved in a direction in which the second compression member 120 is decoupled from the coupling body 300, or the dial knob 420 may be rotated in the counterclockwise direction.

In addition, the insertion guide hole 310 of the coupling body 300 may be provided with a wire guide 320 to guide a connection path of the connecting wire W so that the connecting wire W of the second compression member 120 is connected to the manipulator 400 while being wound on the rotary body 430. The wire guide 320 may be provided to guide the connecting wire W, extending through the second compression member 120, to both side peripheral portions of the insertion guide hole to 310.

In addition, the fixed body 410 may be provided with wire inlets 412 to guide the connecting wire W along a penetration path, so that the connecting wire W extending from the second compression member 120 is wound on the rotary body 430 by passing through the wire inlets 412. The wire inlets 412 may be provided on locations adjacent to the both side peripheral portions of the insertion guide hole 310 while having a shape corresponding to the wire guide 320.

Since the arrangement of the connecting wire W is maintained along a predetermined path by the wire guide 320 and the wire inlets 412, the connecting wire W may be reliably maintained in position, without a problem, such as twisting or entangling, even in a case in which the second compression member 120 is coupled to or decoupled from the coupling body 300.

Figure 5:
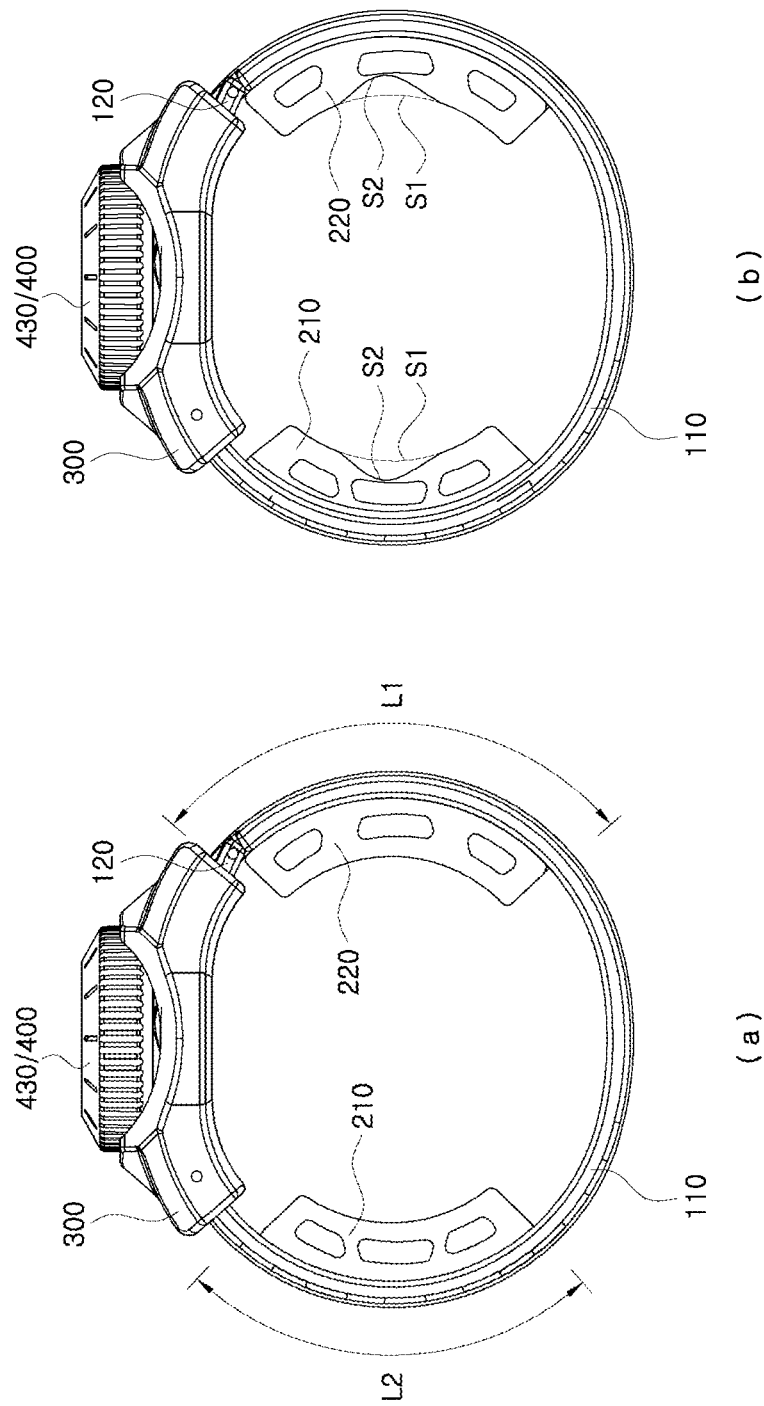
FIG. 5 schematically illustrates various shapes of the compression pads of the wrist guard according to embodiments of the present disclosure.

FIG. 5 schematically illustrates various shapes of the compression pads of the wrist guard according to embodiments of the present disclosure.

As illustrated in FIG. 5, the first compression pad 210 and the second compression pad 220 according to embodiments of the present disclosure may be provided with a variety of shapes.

For example, as illustrated in (a) in FIG. 5, the length L1 of the second compression pad 220 that compresses the area of the ulna H1 may be greater than the length 12 of the first compression pad 210 that compresses the area of the radius H2. The bones constituting an arm include the ulna H1 and the radius H2. In the wrist H, the ulna H1 and the radius H2 protrude outwardly. The ulna H1 is thicker than the radius H2, and has a wider protruding area in the wrist H than the radius H2. Since the area of the ulna H1 is relatively wider, it may be more appropriate to compress the area of the ulna H1 and the area of the radius H2 when the length of the second compression pad 220 compressing the area of the ulna H1 is set to be greater.

In addition, as illustrated in (b) in FIG. 5, the first compression pad 210 and the second compression pad 220 may be configured such that surfaces of longitudinally intermediate portions thereof, to be in contact with the wrist H, may be concavely curved. That is, in a case in which the first compression pad 210 and the second compression pad 220 have a uniform thickness, the surfaces to be in contact with the wrist H may be formed along lines S1 in parallel to the curves of the inner surfaces of the first compression member 110 and the second compression member 120. In contrast, according to embodiments of the present disclosure, the surfaces to be in contact with the wrist H may be formed along lines S2 having a concavely curved shape. Since the surfaces to be in contact width the wrist H are formed to be concavely curved, the first compression pad 210 and the second compression pad 220 may be more closely in contact with the wrist H, thereby more reliably compressing the ulna area and the radius area of the wrist H.

Figure 6:
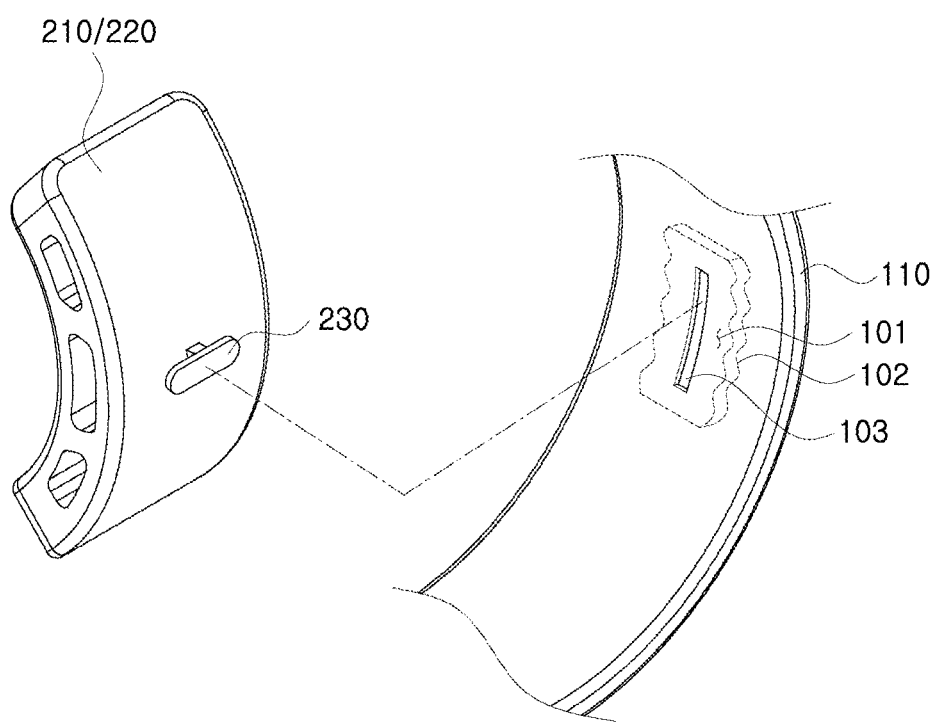
FIGS. 6 and 7 schematically illustrate a compression pad moving structure of the wrist guard according to embodiments of the present disclosure.
Figure 7:
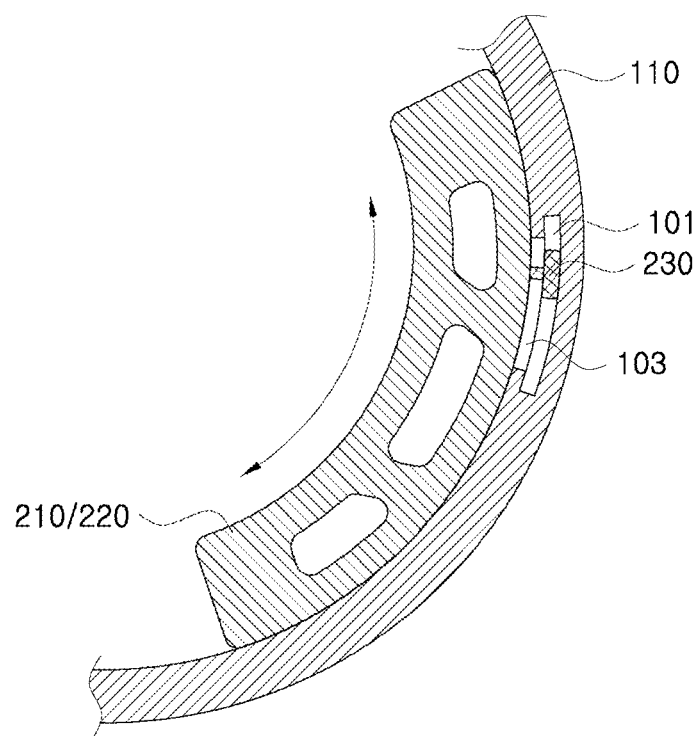

FIGS. 6 and 7 schematically illustrate a compression pad moving structure of the wrist guard according to embodiments of the present disclosure.

As illustrated in FIGS. 6 and 7, the first compression pad 210 and the second compression pad 220 according to embodiments of the present disclosure may be disposed to be movable by predetermined distances in the longitudinal direction of the compression member 100, by which the positions of the first compression pad 210 and the second compression pad 220 are adjustable. Accordingly, the areas of the ulna and the radius, which may differ depending on the user, may be accurately compressed.

When the wrist guard is attached to the wrist H, the first compression pad 210 and the second compression pad 220 are disposed opposite to each other to compress the area of the ulna H1 and the area of the radius H2 of the wrist H. Here, the first compression pad 210 and the second compression pad 220 may not accurately compress intended points of some users, since the shape of the wrist H, the positions of the ulna H1 and the radius H2, and the like may differ depending on the user.

Accordingly, the user may adjust the positions of the first compression pad 210 and the second compression pad 220 to be suitable to him or her by moving the first compression pad 210 and the second compression pad 220. In this manner, the user may locate the first compression pad 210 and the second compression pad 220 at correct positions, whereby the area of the ulna H1 and the area of the radius H2 are accurately compressed.

To move the positions of the first compression pad 210 and the second compression pad 220, each of the surfaces of the first compression pad 210 and the second compression pad 220, in contact with the compression member 100, may be provided with an insertion protrusion 230 that may be inserted into the internal space of the compression member 100. In addition, the compression member 100 is provided with a pad receptacle 101, into which the insertion protrusion 230 is movably inserted. A movement guide 102 is provided in the internal space of the pad receptacle 101, such that the insertion protrusion 230 may be moved by external force while being engaged with movement guide 102. Here, an open portion 103 may be provided in the inner side of each of the compression member 100 to extend in the longitudinal direction, such that the insertion protrusion 230 of each of the first compression pad 210 and the second compression pad 220 is inserted through the open portion 103. The insertion protrusion 230 may be inserted into the pad receptacle 101 through the open portion 103 to be accommodated in the pad receptacle 101, and may move in the longitudinal direction along the movement guide 102 disposed within the pad receptacle 101. Concave-convex portions may be provided on peripheral portions of the movement guide 102, and the insertion protrusion 230 may be moved by external force in a stepwise manner while being engaged with the concave convex portions.

According to the above-described configuration, in a case in which the user has the wrist guard attached to the wrist H, the user may adjust the positions of the first compression pad 210 and the second compression pad 220 by pushing or pulling the first compression pad 210 and the second compression pad 220 in the longitudinal direction, whereby the ulna area and the radius area are accurately compressed.

Figure 8:
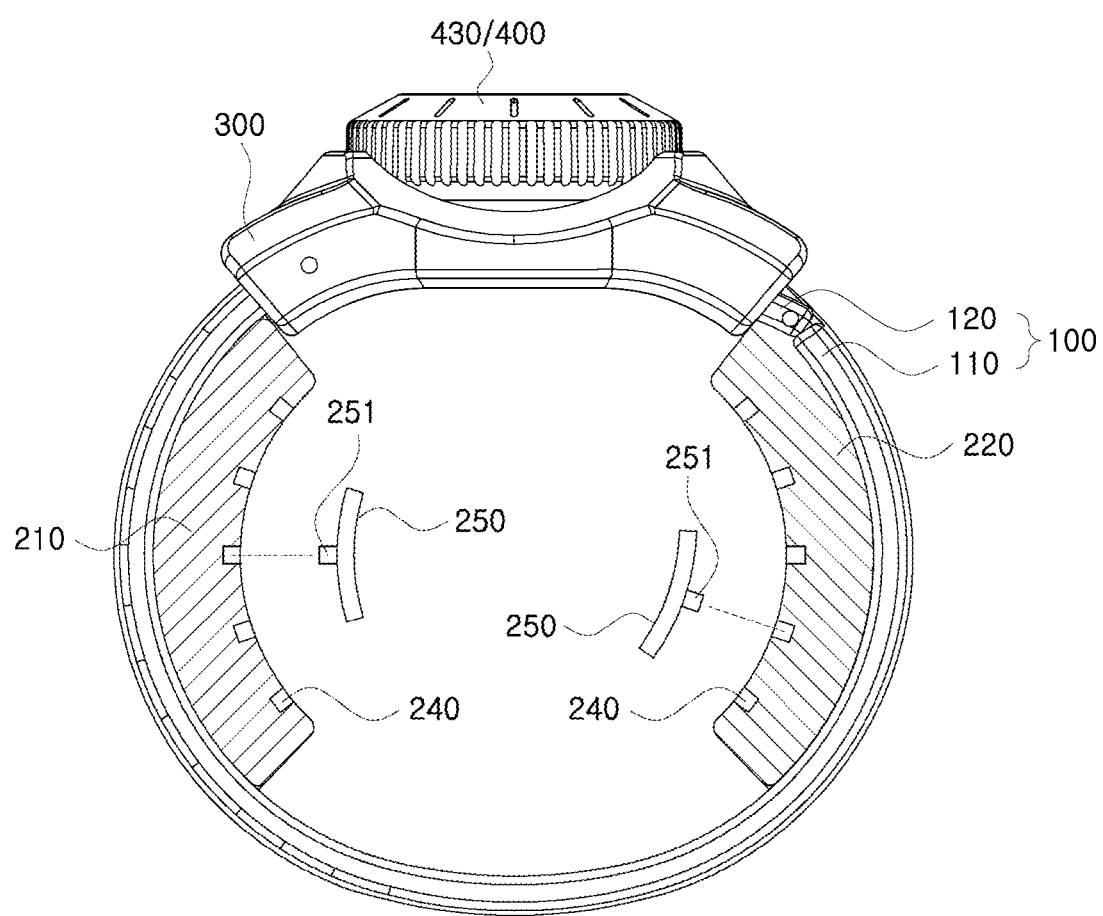
FIG. 8 schematically illustrates a coupling structure for auxiliary compression pads of the wrist guard according to embodiments of the present disclosure.

FIG. 8 schematically illustrates a coupling structure for auxiliary compression pads of the wrist guard according to embodiments of the present disclosure.

As illustrated in FIG. 8, the first compression pad 210 and the second compression pad 220 according to embodiments of the present disclosure may further include auxiliary compression pads 250, respectively.

The auxiliary compression pads 250 may be configured such that the auxiliary compression pads 250 are detachably coupled to the surfaces of the first compression pad 210 and the second compression pad 220, the surfaces being supposed to be in contact with the wrist H. The auxiliary compression pads 250 are configured to be coupled to the surfaces of the first compression pad 210 and the second compression pad 220, the surfaces being supposed to be in contact with the wrist H, such that the auxiliary compression pads 250 substantially compress the area of the ulna H1 and the area of the radius H2 of the wrist H. The auxiliary compression pads 250 may be made of a soft material, such as leather or silicone.

It is possible to adjust the thicknesses of the first compression pad 210 and the second compression pad 220 by coupling or decoupling the auxiliary compression pads 250 to or from the first compression pad 210 and the second compression pad 220. That is, coupling the auxiliary compression pads 250 to the first compression pad 210 and the second compression pad 220 increases the overall thicknesses of the first compression pad 210 and the second compression pad 220, while decoupling the auxiliary compression pads 250 from the first compression pad 210 and the second compression pad 220 reduces the overall thicknesses of the first compression pad 210 and the second compression pad 220.

As described above, it is possible to adjust the overall thicknesses of the first compression pad 210 and the second compression pad 220 using the auxiliary compression pads 250. Accordingly, the user may properly adjust the thicknesses of the first compression pad 210 and the second compression pad 220 depending on the body conditions of the user or the environmental conditions.

Here, the surfaces of the first compression pad 210 and the second compression pad 220, to be in contact with the wrist H, may have fitting holes 240. A fitting protrusion 251 may be provided on one surface of each of the auxiliary compression pads 250 so as to be fitted into the fitting holes 240. In response to the coupling of the fitting protrusions 251 and the fitting holes 240, the auxiliary compression pads 250 may be detachably coupled to the first compression pad 210 and the second compression pad 220.

In addition, it is possible to adjust the positions of the portions substantially compressing the ulna area and the radius area adjusting the locations to which the auxiliary compression pads 250 are coupled. In this regard, the plurality of coupling holes 240 may be provided in each of the first compression pad 210 and the second compression pad 220 in the longitudinal direction.

That is, as illustrated in FIG. 8, the coupling positions of the auxiliary compression pads 250 may be adjusted by selectively coupling the fitting protrusion 251 of each of the auxiliary compression pads 250 to one of the plurality of coupling holes 240 in each of the first compression pad 210 and the second compression pad 220. According to this structure, the locations of the wrist H to be compressed by the auxiliary compression pads 250 may be conveniently adjusted.

The foregoing descriptions have been presented in order to explain certain principles of the present disclosure by way of example. A person having ordinary knowledge in the art to which the present disclosure relates could make various modifications and variations without departing from the essential features of the present disclosure. The foregoing embodiments disclosed herein shall be interpreted as being illustrative, while not being limitative, of the principle and scope of the present disclosure. It should be understood that the scope of the present disclosure shall be defined by the appended Claims and all of their equivalents fall within the scope of the present disclosure.

The invention claimed is:

1. A wrist guard attached to a wrist to protect the wrist, the wrist guard comprising:
 a compression member surrounding a wrist, wherein a first compression pad is provided on one portion of an inner surface of the compression member to be able to compress one of an ulna area and a radius area of the wrist toward a central portion of the wrist, and a second compression pad is provided on an opposite side portion of the inner surface of the compression member to be able to compress other side of the ulna area and the radius area of the wrist toward the central portion of the wrist;
 a coupling body, wherein one end portion of the compression member is pivotably coupled to one portion of the coupling body, and another opposite end portion of the compression member is coupled to or decoupled from other end portion of the coupling body in response to user operation,
 wherein the wrist, other than the ulna area and the radius area, is not compressed, and a coupling state of the second compression member is adjustable by the user operation so that compressive load of the compression member on the ulna area and the radius area is adjustable;
 wherein the compression member includes: a main ring body made of an elastically deformable material and having a shape of a ring with one open portion, the first compression pad and the second compression pad being mounted on inner surface portions of the main ring body, wherein one end portion of the main ring body is pivotably coupled to one portion of the coupling body; a connecting body pivotably coupled to other end portion of the main ring body, wherein the connecting body is coupled to or decoupled from the other portion of the coupling body;

wherein the other end portion of the coupling body has an insertion guide hole allowing the another opposite end portion of the compression member to be inserted thereinto and coupled thereto, a manipulator operable by a user is disposed on a central portion of the coupling body, and a depth, to which the another opposite end portion of the compression member is inserted into the insertion guide hole, is adjustable by the manipulator and wherein a connecting wire is coupled to, while extending through, a distal end of the connecting body, and the connecting wire is pulled by operating the manipulator, so that the connecting body is inserted into and coupled to the insertion guide hole.

2. The wrist guard according to claim 1, wherein the connecting body is made of a rigid material that is less elastically deformable than the main ring body.

3. The wrist guard according to claim 1, wherein the connecting body has a guide through-hole to guide a path along which the connecting wire is coupled to, while extending through, the connecting body, and the guide through-hole has a curved path convex in a direction opposite to a pulling direction of the connecting wire.

4. The wrist guard according to claim 1, wherein the manipulator includes:

a fixed body fixedly coupled to the coupling body and having a ratchet provided on an inner circumferential portion of a top end portion thereof;

a rotary body coupled to the fixed body so as to be movable and rotatable in a top-bottom direction and having a stopper protrusion provided on one portion thereof, wherein the stopper protrusion engages with the ratchet to restrain unidirectional rotation in downward movement, and engagement of the stopper protrusion and the ratchet is released in upward movement so as to enable bidirectional rotation; and a dial knob coupled to an upper portion of the rotary body to move in a top-bottom direction and rotate together with the rotary body, the dial knob being operable by the user, wherein the connecting wire coupled to, while extending through, the connecting body is wound on the rotary body in a single direction.

5. The wrist guard according to claim 1, wherein the first compression pad and the second compression pad extend along predetermined longitudinal portions of the compression member, with through-holes penetrating through central portions of the first and second compression pads in a transverse direction.

6. The wrist guard according to claim 1, wherein plurality of through-holes of the first and second compression pads are spaced apart from each other in a longitudinal direction of the compression member.

* * * * *